(12) United States Patent
Peng et al.

(10) Patent No.: US 9,797,874 B2
(45) Date of Patent: Oct. 24, 2017

(54) OPTICAL TESTING SYSTEM AND METHOD

(71) Applicant: China Agricultural University, Beijing (CN)

(72) Inventors: Yankun Peng, Beijing (CN); Juan Zhao, Beijing (CN)

(73) Assignee: China Agricultural University, Beijing (CN)

( * ) Notice: Subject to any disclaimer, the term of this patent is extended or adjusted under 35 U.S.C. 154(b) by 185 days.

(21) Appl. No.: 14/830,365

(22) Filed: Aug. 19, 2015

(65) Prior Publication Data

US 2016/0169793 A1 Jun. 16, 2016

(30) Foreign Application Priority Data

Dec. 15, 2014 (CN) .......................... 2014 1 0778537

(51) Int. Cl.
| | |
|---|---|
| *G01N 21/25* | (2006.01) |
| *G01N 33/12* | (2006.01) |
| *G01N 21/31* | (2006.01) |
| *G01N 21/47* | (2006.01) |
| *G01J 3/10* | (2006.01) |
| *G01J 3/12* | (2006.01) |

(52) U.S. Cl.
CPC ................ *G01N 33/12* (2013.01); *G01J 3/10* (2013.01); *G01N 21/255* (2013.01); *G01N 21/31* (2013.01); *G01N 21/474* (2013.01); *G01J 2003/1282* (2013.01); *G01N 2021/4742* (2013.01); *G01N 2201/0627* (2013.01); *G01N 2201/129* (2013.01)

(58) Field of Classification Search
CPC ...... G01N 33/12; G01N 21/255; G01N 21/31; G01N 21/474; G01N 2201/0627; G01N 2201/129; G01N 2021/4742; G01J 3/10; G01J 2003/1282
See application file for complete search history.

(56) References Cited

U.S. PATENT DOCUMENTS

| | | | |
|---|---|---|---|
| 5,838,451 A * | 11/1998 | McCarthy ............. | G01J 3/2803 356/402 |
| 2015/0192521 A1* | 7/2015 | Lausch ................ | G01N 33/521 250/459.1 |

* cited by examiner

*Primary Examiner* — Tony Ko
(74) *Attorney, Agent, or Firm* — Panitch Schwarze Belisario & Nadel LLP

(57) ABSTRACT

An optical testing system includes: a testing probe, a collecting unit, and a processing unit, wherein the testing probe includes a plurality of spectrum photodiodes used for emitting and casting monochromatic light to a sample, wherein the wavelength of the light emitted by at least one spectrum photodiode is different from that of any other. The collecting unit collects multi-way signal light obtained after the emitted monochromatic light is reflected by the sample surface. The processing unit includes a photoelectric conversion module, an adding module and a testing module. The photoelectric conversion module converts the collected multi-way signal light respectively to multi-way electrical signals. The adding module performs an adding operation for the multi-way electrical signal to obtain an operation result. The testing module tests a quality parameter of the sample according to the operation result, and outputs a testing result.

7 Claims, 4 Drawing Sheets

OPTICAL TESTING SYSTEM AND METHOD

The present invention relates to the field of testing techniques, and particularly relates to an optical testing system and method.

BACKGROUND OF THE INVENTION

With steady improvement of the living standard, increasing consumption demands, relative change of dietary pattern and more and more attention to health, people's demands for fresh raw meat are being more diversified, and people are more demanding for the quality and safety of fresh raw meat. Since the fresh raw meat is rich in nutrient and water, easy to be rotten, and the process of slaughtering and marketing of such meat is not so clean, it is difficult to guarantee the quality of such meat; therefore, it is very important and urgent to well test and monitor the quality of such meat.

The traditional method for testing such meat is low in testing efficiency, long in the time required, and big in the destruction of the product. As a new technology developed in recent years, the nondestructive testing technology means using a method whereby the quality of a sample is appraised while the sample is not destroyed. The spectrum technology is the one often used for nondestructively testing such meat, but such testing of samples mainly depends on a spectrometer which is the main necessary part for testing; however, most spectrometers on the market are high in cost, great in volume, and high in maintenance cost, incapable of being widely used in the practical operation for testing the quality of raw fresh meat.

With rapid development of optical technology, the intelligent testing system for farm products is developing towards portability, handheld type, miniaturization, microminiaturization and intellectualization. It is extremely important to develop simple, rapid, and light testing equipment, and it is an inevitable trend of development to be based on the research results in the laboratories and not to use expensive or large equipment.

BRIEF SUMMARY OF THE INVENTION

The present invention provides an optical testing system and method, allowing the quality of fresh raw meat to be tested rapidly, cheaply, and nondestructively.

The present invention first provides an optical testing system, including: a testing probe, a collecting unit, and a processing unit, wherein said testing probe comprises a plurality of spectrum photodiodes, each of said spectrum photodiodes is used for emitting monochromatic light, and casting said monochromatic light to a sample, wherein the wave length of the monochromatic light emitted by at least one spectrum photodiode is different from that of any other spectrum photodiode;

said collecting unit is used for collecting multi-way signal light obtained after the monochromatic light emitted by said plurality of spectrum photodiodes is reflected by said sample surface;

said processing unit includes a photoelectric conversion module, an adding module and testing module, said photoelectric conversion module being used for converting the multi-way signal light collected by said collecting unit respectively to multi-way electrical signals; said adding module being used for performing an adding operation for said multi-way electrical signals to obtain an operation result; said testing module being used for testing a quality parameter of said sample according to said operation result, and outputting a testing result.

Further, said testing probe is further used for choosing the characteristic wavelength of said spectrum photodiode according to the quality parameter type of the sample to be tested.

Further, each spectrum photodiode includes a reflected light outgoing hole, said reflected light outgoing hole being connected with an optical fiber, said optical fiber being used for collecting the signal light obtained after reflection by said sample surface and transmitting the signal light to said collecting unit.

Further, said reflected light outgoing hole is located in the central position of said spectrum photodiode.

Further, said adding module includes: an operational amplifier;

said adding module is further used for performing an amplification operation for said multi-way electrical signals.

On the other hand, the present invention further provides an optical testing method for optical testing by using any optical testing system as mentioned above, including the steps of:

casting multi-way monochromatic light to a sample surface;

receiving multi-way signal light obtained by reflection of said multi-way monochromatic light by said sample surface;

converting said multi-way signal light respectively to multi-way electrical signals;

performing an adding operation for said multi-way electrical signals to obtain an operation result;

testing a quality parameter of said sample according to said operation result, and outputting a testing result.

Further, the step of converting said multi-way signal light respectively to multi-way electrical signals includes the steps of converting n ways of signal light $S_1, S_2, \ldots, S_n$ to n ways of voltage signals $V_1, V_2, \ldots, V_n$ after photoelectric conversion;

said step of performing an adding operation for said multi-way electrical signals to obtain an operation result including the step of:

performing an adding operation for said n ways of voltage signals $V_1, V_2, \ldots, V_n$ to obtain the operation result y:

$$y = c + k_1 V_1 + k_2 V_2 + \ldots + k_n V_n,$$

wherein c is a constant, depending on testing conditions and testing environment, and $\{k_1, k_2, \ldots, k_n\}$ is the coefficient matrix to which said n ways of voltage signals correspond;

said step of testing a quality parameter of said sample according to said operation result and outputting a testing result including the step of:

comparing said operation result y with a predetermined threshold value corresponding to the quality parameter to be tested of said sample: when said operation result y is within the range of said predetermined threshold value, regarding the corresponding quality of said sample as good; otherwise, regarding the corresponding quality of said sample as not good.

It is thus evident that in the optical testing system and method provided by the present invention, it is possible to choose a spectrum photodiode to which the characteristic wavelength corresponding to the quality parameter to be tested in the sample corresponds, acquire the reflected signal light of a plurality of characteristic wave lengths by using monochromatic lights emitted by spectrum photodiodes, and test the quality parameter of the sample after the multi-way signal light is processed, thus solving the problem in the prior art that the testing by spectrum technology is high in cost and cannot be widely used.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Figure 1:
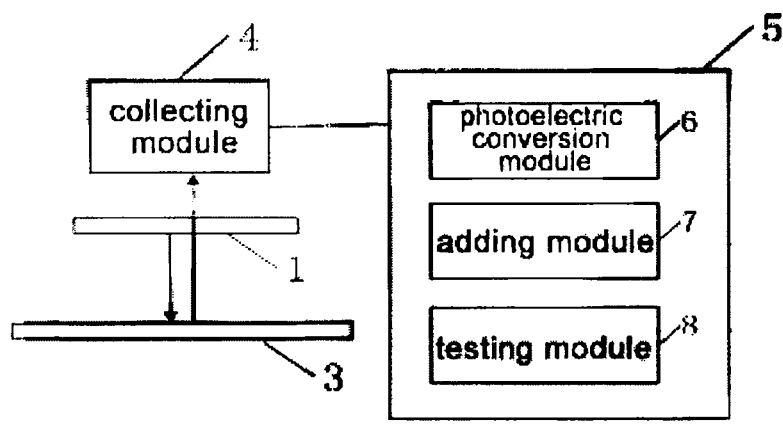
FIG. 1 is a side view of an optical testing system in one embodiment of the present invention.
Figure 2:
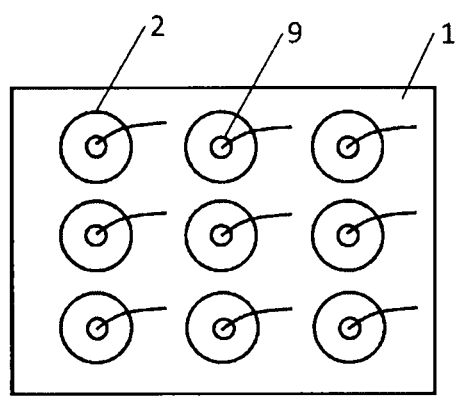
FIG. 2 is a structural schematic diagram of a testing probe of an optical testing system in one embodiment of the present invention.

Shown in FIG. 1 is a side view of an optical testing system of this embodiment, and shown in FIG. 2 is a structural schematic diagram of a testing probe of an optical testing system in the embodiment of the present invention. As shown in FIGS. 1 and 2, this embodiment specifically includes:

a testing probe 1, including a plurality of spectrum photodiodes 2, each spectrum photodiode 2 is used for emitting monochromatic light and casting said monochromatic light to a sample 3, wherein the wave length of the monochromatic light emitted by at least one spectrum photodiode is different from that of any other spectrum photodiode;

a collecting unit 4 being used for collecting multi-way signal light obtained after the monochromatic light emitted by the plurality of spectrum photodiodes 2 is reflected by the surface of sample 3;

a processing unit 5 including a photoelectric conversion module 6, an adding module 7 and a testing module 8: the photoelectric conversion module 6 being used for converting multi-way signal light collected by the collecting unit 4 respectively to multi-way electrical signals; an adding module 7 being used for performing an adding operation for the multi-way electrical signals to obtain an operation result; a testing module 8 being used for testing a quality parameter of the sample 3 according to the operation result, and outputting a testing result.

The testing probe 1 is capable of choosing a spectrum photodiode 2 of different characteristic wavelength according to the quality parameter type of the sample to be tested, and spectrum photodiodes of n wavebands form a testing array to obtain a more pertinent and more exact testing result.

Figure 3:
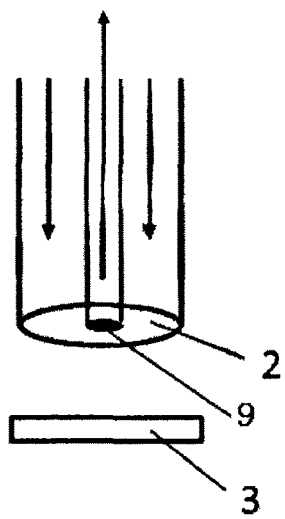
FIG. 3 is a longitudinal sectional view of a spectrum photodiode of an optical testing system in one embodiment of the present invention.

In addition, each spectrum photodiode 2 may include a reflected light outgoing hole 9. FIG. 3 is a longitudinal sectional view of a spectrum photodiode, each reflected light outgoing hole 9 may be connected with an optical fiber (not shown in the figure), the optical fiber being used for collecting the signal light obtained after reflection by the surface of sample 3 and transmitting the signal light to the collecting unit 4. For example, the reflected light outgoing hole 9 of may be located in the central position of the spectrum photodiode 2.

In a specific structure of this embodiment, the adding module 7 may include an operational amplifier; the adding module 7 may further be used for performing an amplification operation for the multi-way electrical signals.

Figure 4:
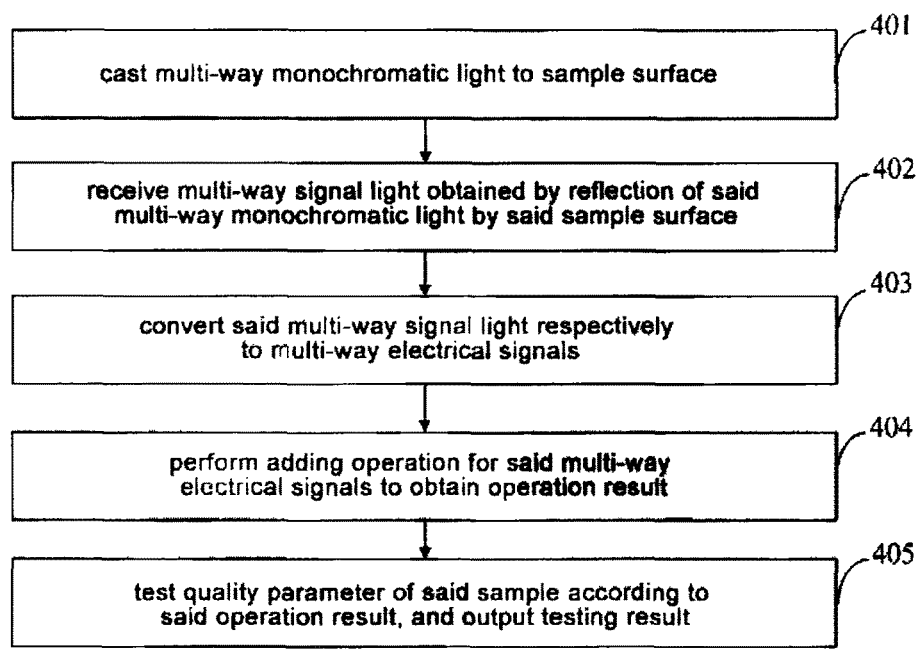
FIG. 4 is a schematic diagram showing steps of an optical testing method in one embodiment of the present invention.

Shown in FIG. 4 is an optical testing method for optical testing by using an optical testing system according to any of the aforesaid embodiments; as shown in FIG. 4, the method of this embodiment includes the steps:

Step 401: the system casts multi-way monochromatic light to a sample surface.

Step 402: the system receives the multi-way signal light obtained by reflection of said multi-way monochromatic light by said sample surface.

For example, n ways of signal light $S_1, S_2, \ldots, S_n$ may be obtained by reflection of the n ways of monochromatic light emitted by n spectrum photodiodes by the sample surface.

Step 403: the system converts said multi-way signal light respectively to multi-way electrical signals.

In the aforesaid application situation of this embodiment, the system may convert the n ways of signal light $S_1, S_2, \ldots, S_n$ to n ways of voltage signals $V_1, V_2, \ldots, V_n$ after photoelectric conversion.

Step 404: the system performs an adding operation for said multi-way electrical signals to obtain an operation result.

Figure 5:
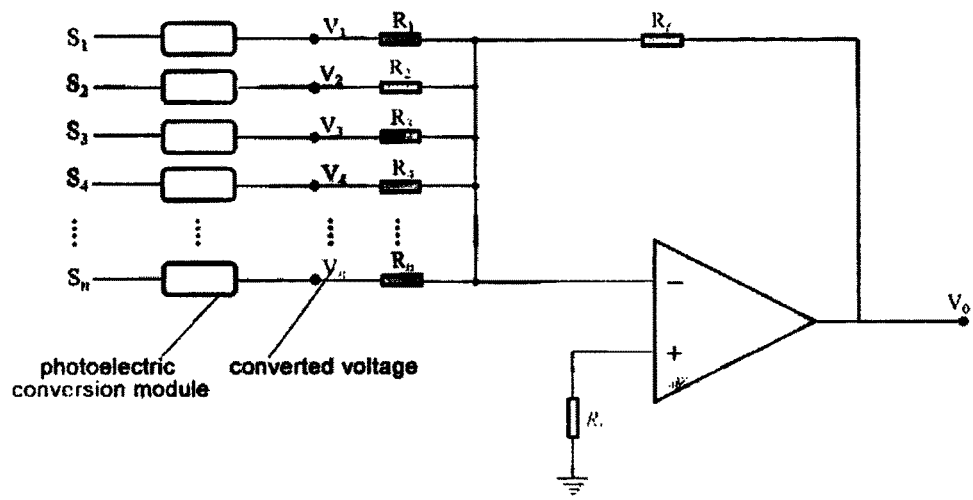
FIG. 5 is a schematic flowchart of processing signal light in an optical testing method in one embodiment of the present invention.

In the aforesaid situation of this embodiment, the system may perform an adding operation for said n ways of voltage signals $V_1, V_2, \ldots, V_n$ to obtain the operation result y:

$$y = c + k_1 V_1 + k_2 V_2 + \ldots + k_n V_n,$$

wherein c is a constant, depending on testing conditions and testing environment, $\{k_1, k_2, \ldots, k_n\}$ is the coefficient matrix to which said n ways of voltage signals correspond, and the specific operation process may be seen in FIG. 5.

The case of determining the main parameter for the safety quality of fresh raw meat, namely the total viable count (TVC) will be taken as an example:

The tested sample is the longissimus dorsi of fresh raw pork bought from a supermarket which is cut into pieces of 8 cm in length, 5 cm in width, and 2.5 cm in thickness. There are 89 pieces of tested samples altogether including 66 pieces in the calibration set, and 23 pieces in the validation set with a proportion of 3:1 to build a model for predicting the total viable count in pork.

Figure 6:
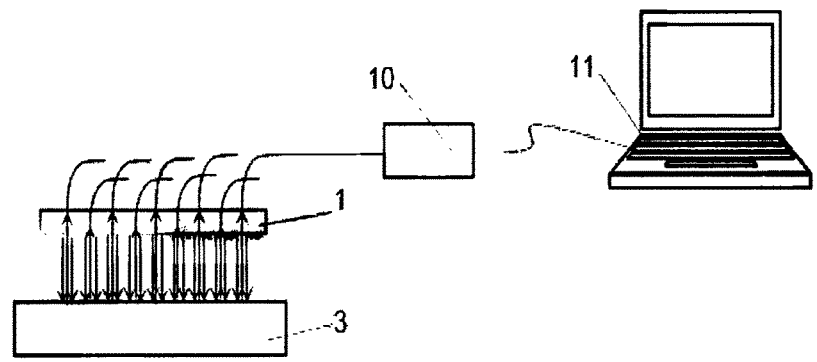
FIG. 6 is a schematic diagram of a sample testing system used in an optical testing method in one embodiment of the present invention.

The sample reflection information is acquired by using the testing system as shown in FIG. 6. As shown in FIG. 6, the reflection information of the sample 3 acquired by each spectrum photodiode is obtained by using the testing probe 1 which is the same as the one shown in FIG. 2 in structure and wave band and by using the optical fiber in the collecting unit 4 which is connected to a VIS/NIR spectrometer 10, and saved visually in a computer 11. The spectrum photodiode of each characteristic wave band has a certain half-wave bandwidth, so the acquired reflection information is only the information roughly within a certain range of wave bandwidth under that characteristic waveband.

The characteristic wavelengths determined for the TVC in fresh raw pork include those of 466, 508, 547, 586, 615, 717, 850, and 955 nm. For each point on each sample, the spectrums under 8 different wavelengths are measured and averaged, and the average of those at 8 different points of the sample tested in an experiment is taken as spectrum information of that sample.

Figure 7:
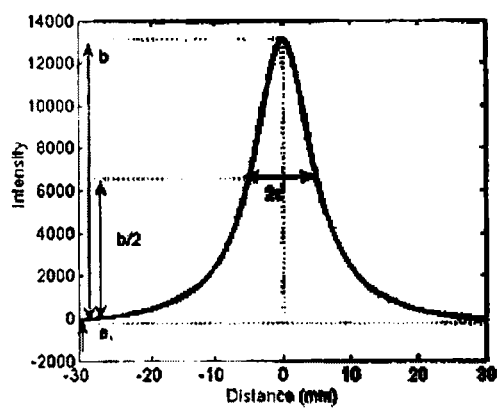
FIG. 7 is a schematic diagram of a Lorentzian function of an optical testing method in one embodiment of the present invention.
Figure 8:
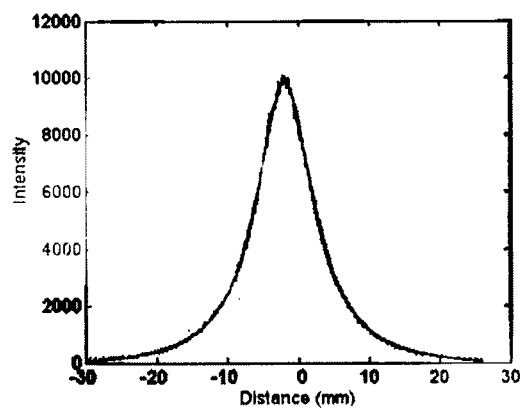
FIG. 8 is a schematic diagram of the single-wavelength fitting results of a Lorentzian function of an optical testing method in one embodiment of the present invention.

The characteristic spectrum may be obtained by fitting the curve acquired under each wavelength; the characteristic spectrum is used to replace the original spectrum information, so that the data size is small, and comprehensive information of the sample can be reflected. The diffusion fitting method may be a Lorentzian function fitting, as shown in FIG. 7, and the expression of the Lorentzian function is as follows:

$$I = a + \frac{b}{1 + (x/c)^2}$$

wherein I is the light reflection intensity at any point on the scattering curve; x is the distance between that point and the light incidence point (curve center point); a is the asymptotic value of the Lorentzian distribution curve; b is the peak value of the Lorentzian curve at the point where x=0; c is the full-wave bandwidth of the scattering curve, namely the bandwidth of the scattering curve at the point where the reflection value is b/2 the peak value; and the single-wavelength fitting results of the Lorentzian function can be seen in FIG. 8.

Figure 9:
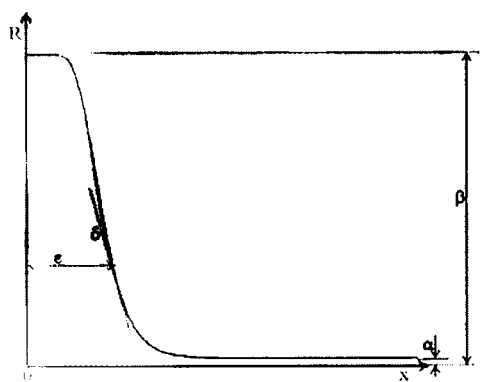
FIG. 9 is a schematic diagram of a Lorentzian four parameter distribution function of an optical testing method in one embodiment of the present invention.

In the embodiment above, the fitting method is not limited to the one by using the Lorentzian function; the four parameters of the Gompertz function may also be used for data analysis, as shown in FIG. 9; for various parameters of the tested sample (such as freshness, water content, and TVC), a more suitable fitting method may also be selected.

$$R = \alpha + \beta(1 - e^{-exp(\epsilon - \delta z)})$$

wherein R is corrected reflection intensity, $\alpha$ is the asymptotic value of the Gompertz distribution curve; $\beta$ is the upper limit value of the estimated light intensity of the Gompertz distribution curve at the point where x=0; $\epsilon$ is the full scattering width of the Gompertz curve at the inflection point; $\delta$ is the slope ratio of the Gompertz curve at the inflection point; and x is the distance between that point and the light incidence point (curve center point). In embodiments of the present invention, the data method for acquiring a coefficient matrix after the fitting will be introduced, by taking the case of testing the TVC in fresh raw meat and the case of Lorentzian function fitting as an example. The Lorentzian function fitting is made at each wavelength by using the nonlinear regression method, so the spectrum curve under each waveband may be described by the three parameters a, b, and c of the Lorentzian function. After the fitting of the spectrum curve at all wavelengths is complete, the three parameters a, b, and c of the fitting function form a "characteristic spectrum" respectively, and, for the characteristic parameters, the combinations of a&b, a&c, b&c, and a&b&c may be made to form a characteristic spectrum matrix.

The single parameter an analysis/modeling is taken as an example to illustrate the specific method of application. When the characteristic wavelengths include those of 466, 508, 547, 586, 615, 717, 850, and 955 nm, the Lorentzian a parameter characteristic matrix [a] is obtained.

The multiple linear regression method is used:

$$y_i = \beta_0 \beta_1 X_{i1} + \ldots \beta_p X_{ip} + \epsilon i (i=1,2,\ldots,n)$$

where $\epsilon i$ is the random error in measurement. It is commonly supposed that E $(\epsilon i)=0$, D $(\epsilon i)=\sigma 2$, and $\epsilon 1$, $\epsilon 2, \ldots$, en are independent from each other.

The above expression may be written as a matrix: $Y = X\beta + \epsilon$ $$X = \begin{pmatrix} 1 & a_1 & a_2 & \ldots & a_p \end{pmatrix}$$

wherein $$\beta = (X'X)^{-1} X'Y$$

$$\beta = \begin{pmatrix} k_0 \\ k_1 \\ k_2 \\ \vdots \\ k_n \end{pmatrix}$$

wherein X is a parameter matrix, $a_p$ being the fitting parameter a value at the p'th characteristic wavelength, $\beta$ being a coefficient matrix, c being a constant term, $k_n$ being the n'th predicting coefficient, Y being the actual value of the TVC on the tested sample surface as measured by using the standard GB/T4789.2-2010. A Lorentzian function fitting is made for the 66×i spectrum curves of the 66 samples in the calibration set, and a multiple linear regression modeling is made by using i characteristic wavebands. $\beta$ is the prediction coefficient matrix obtained after multiple linear regression modeling is made.

After the modeled prediction coefficient matrix is obtained, the TVC prediction may be made for each sample to be tested.

Step 405: the system tests the quality parameter of said sample according to said operation result, and outputs the testing result.

In the above situation, the system may compare operation result y with a predetermined threshold value corresponding to the quality parameter to be tested of said sample: when operation result y is within the range of said predetermined threshold value, the corresponding quality of said sample is regarded as good; otherwise, the corresponding quality of said sample is regarded as not good. The predetermined threshold value corresponding to a quality parameter may be determined according to the standard established by the state or a corresponding organization.

For example, in case of testing TVC for the safety quality of fresh raw meat in step 404, wherein the sample is a piece of meat of 8 cm in length, 5 cm in width, and 2.5 cm in thickness, the light scattering signals $S_1, S_2, \ldots, S_8$ at 8 characteristic wavebands for that piece of meat are tested and received at a time. After 8 light signals are converted by the photoelectric module of the processing unit, 8 ways of voltage signals $V_1, V_2, \ldots, V_8$ are output.

After the coefficient matrix of the known prediction model is obtained, in the processing unit of the system, a different resistance value is selected in the part of operational circuit design according to the different weighted proportion coefficient $\beta_p$ value to which the different characteristic waveband corresponds.

$$k_1 = -\frac{R_f}{R_1} \quad k_2 = -\frac{R_f}{R_2} \quad k_n = -\frac{R_f}{R_n}$$

$$V_{01} = -\frac{R_f}{R_1}V_1 \quad V_{02} = -\frac{R_f}{R_2}V_2 \quad V_{0n} = -\frac{R_f}{R_n}V_n$$

$$V_0 = V_{01} + V_{02} + \ldots + V_{0n}$$

$$V_0 = -\left(\frac{R_f}{R_1}V_1 + \frac{R_f}{R_2}V_2 + \ldots \frac{R_f}{R_n}V_n\right)$$

wherein $R_f$ is a feedback resistance, $R_p$ is a compensating resistance, $R_i$, is an input resistance, $V_0$ is an output resistance. $R_p=R_1//R_2// \ldots //R_n$, n output resistances being connected in parallel.

The prediction value of TVC as actually obtained is $y=c-V_0$; since c is a constant term, the maximum TVC in fresh (cold) meat shall not exceed $1\times10^6$ CFU/g specified in the state standard as the threshold for testing. Therefore, in the present invention, the actual testing threshold is (6–c) log CFU/g. If the TVC in the tested meat sample as predicted is greater than the set threshold value, it is determined as unqualified; otherwise, it is determined as qualified.

It is thus evident that in the optical testing system and method provided by the embodiments of the present invention, it is possible to choose a spectrum photodiode to which the characteristic wavelength corresponding to the quality parameter to be tested in the sample corresponds, acquire the reflected signal light of a plurality of characteristic wavelengths by using monochromatic lights emitted by spectrum photodiodes, and test the quality parameter of the sample after the multi-way signal light is processed, thus solving the problem in the prior art that testing by spectrum technology is high in cost and cannot be widely used.

Finally, it should be noted that the above embodiments are only for illustrating the technical solutions of the present invention; however, the present invention is not limited thereto. Although the present invention has been described in detail with reference to the foregoing embodiments, those skilled in the art should understand that various modifications to the technical solutions described in the foregoing embodiments or equivalent substitutions to part of the technical features therein can still be made by the person skill in the art, and such modifications or substitutions should not make the essence of the corresponding technical solutions depart from the spirit and scope of the technical solutions in the embodiments of the present invention.

We claim:

1. An optical testing system, comprising: a testing probe, a collecting unit, and a processing unit, wherein
    said testing probe comprises a plurality of spectrum photodiodes, each of said spectrum photodiode is used for emitting monochromatic light, and casting said monochromatic light to a sample, wherein the wave length of the monochromatic light emitted by at least one spectrum photodiode is different from that of any other spectrum photodiode;
    said collecting unit is used for collecting multi-way signal light obtained after the monochromatic light emitted by said plurality of spectrum photodiodes is reflected by said sample surface;
    said processing unit comprises a photoelectric conversion module, an adding module and testing module, said photoelectric conversion module being used for converting the multi-way signal light collected by said collecting unit respectively to multi-way electrical signals; said adding module being used for performing an adding operation for said multi-way electrical signals to obtain an operation result; said testing module being used for testing a quality parameter of said sample according to said operation result, and outputting a testing result,
    wherein each spectrum photodiode comprises a reflected light outgoing hole, said reflected light outgoing hole being connected with an optical fiber, said optical fiber being used for collecting the signal light obtained after reflection by said sample surface and transmitting the signal light to said collected unit.

2. An optical testing system according to claim 1, wherein said testing probe is further used for
    choosing a spectrum photodiode of said characteristic wave band according to the quality parameter type of the sample to be tested.

3. An optical testing system according to claim 1, wherein said reflected light outgoing hole is located in the central position of said spectrum photodiode.

4. An optical testing system according to claim 1, wherein said adding module comprises an operational amplifier;
    said adding module is further used for performing an amplification operation for said multi-way electrical signals.

5. An optical testing method, wherein the optical testing system according to claim 1 is used for optical testing, comprising the steps of:
    casting multi-way monochromatic light to a sample surface;
    receiving the multi-way signal light obtained by reflection of said multi-way monochromatic light by said sample surface;
    converting said multi-way signal light respectively to multi-way electrical signals;
    performing an adding operation for said multi-way electrical signals to obtain an operation result;
    testing a quality parameter of said sample according to said operation result, and outputting a testing result.

6. An optical testing method according to claim 5, wherein
    the step of converting said multi-way signal light respectively to multi-way electrical signals comprises the steps of
    converting n ways of signal light $S_1, S_2, \ldots, S_n$ to n ways of voltage signals $V_1, V_2, \ldots, V_n$ after photoelectric conversion;
    said step of performing an adding operation for said multi-way electrical signals to obtain an operation result comprising the steps of:
    performing an adding operation for said n ways of voltage signals $V_1, V_2, \ldots, V_n$ to obtain the operation result y:

$$y = c + k_1 V_1 + k_2 V_2 + \ldots + k_n V_n,$$

wherein c is a constant, depending on testing conditions and testing environment, and $\{k_1, k_2, \ldots k_n\}$ is the coefficient matrix to which said n ways of voltage signals correspond;

said step of testing a quality parameter of said sample according to said operation result and outputting a testing result comprising the step of:

comparing said operation result y with a predetermined threshold value corresponding to the quality parameter to be tested of said sample: when said operation result y is within the range of said predetermined threshold value, regarding the corresponding quality of said sample as good; otherwise, regarding that the corresponding quality of said sample as not good.

7. An optical testing method, wherein an optical testing system includes a testing probe, a collecting unit, and a processing unit, wherein said testing probe comprises a plurality of spectrum photodiodes, each of said spectrum photodiode is used for emitting monochromatic light, and casting said monochromatic light to a sample, wherein the wave length of the monochromatic light emitted by at least one spectrum photodiode is different from that of any other spectrum photodiode, said collecting unit is used for collecting multi-way signal light obtained after the monochromatic light emitted by said plurality of spectrum photodiodes is reflected by said sample surface, and said processing unit includes a photoelectric conversion module, an adding module and testing module, said photoelectric conversion module being used for converting the multi-way signal light collected by said collecting unit respectively to multi-way electrical signals; said adding module being used for performing an adding operation for said multi-way electrical signals to obtain an operation result; said testing module being used for testing a quality parameter of said sample according to said operation result, and outputting a testing result, the method comprising:

casting multi-way monochromatic light to a sample surface;

receiving the multi-way signal light obtained by reflection of said multi-way monochromatic light by said sample surface;

converting said multi-way signal light respectively to multi-way electrical signals;

performing an adding operation for said multi-way electrical signals to obtain an operation result;

testing a quality parameter of said sample according to said operation result, and outputting a testing result, wherein:

the step of converting said multi-way signal light respectively to multi-way electrical signals comprises the steps of converting n ways of signal light $S_1, S_2, \ldots, S_n$ to n ways of voltage signals $V_1, V_2, \ldots, V_n$ after photoelectric conversion;

said step of performing an adding operation for said multi-way electrical signals to obtain an operation result comprising the steps of:

performing an adding operation for said n ways of voltage signals $V_1, V_2, \ldots, V_n$ to obtain the operation result y:

$$y = c + k_1 V_1 + k_2 V_2 + \ldots + k_n V_n,$$

wherein c is a constant, depending on testing conditions and testing environment, and $\{k_1, k_2, \ldots k_n\}$ is the coefficient matrix to which said n ways of voltage signals correspond;

said step of testing a quality parameter of said sample according to said operation result and outputting a testing result comprising the step of:

comparing said operation result y with a predetermined threshold value corresponding to the quality parameter to be tested of said sample: when said operation result y is within the range of said predetermined threshold value, regarding the corresponding quality of said sample as good; otherwise, regarding that the corresponding quality of said sample as not good.

* * * * *